US008048130B2

(12) United States Patent
Nesper et al.

(10) Patent No.: US 8,048,130 B2
(45) Date of Patent: **\*Nov. 1, 2011**

(54) IMPLANT FOR FIXING BONE PLATES

(75) Inventors: Markus Nesper, Tuttlingen (DE); Klaus-Dieter Steinhilper, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 98 days.

This patent is subject to a terminal disclaimer.

(21) Appl. No.: 12/512,412

(22) Filed: Jul. 30, 2009

(65) Prior Publication Data

US 2009/0292319 A1    Nov. 26, 2009

Related U.S. Application Data

(63) Continuation of application No. 10/911,982, filed on Aug. 4, 2004, now Pat. No. 7,670,361, which is a continuation-in-part of application No. 10/718,851, filed on Nov. 20, 2003, now Pat. No. 7,238,188, which is a continuation of application No. PCT/EP02/05653, filed on May 23, 2002.

(51) Int. Cl.
*A61B 17/66*     (2006.01)

(52) U.S. Cl. ...................................... 606/282

(58) Field of Classification Search .......... 606/328, 606/331, 324, 282, 903, 297, 228, 300, 75, 606/74, 151, 213, 215, 216, 232, 103; 24/129 R, 24/712.1, 712.5, 115 H, 129 A, 130, 68 F, 24/115 R, 127

See application file for complete search history.

(56) References Cited

U.S. PATENT DOCUMENTS

| 261,501 A | * | 7/1882 | Vandermark .............. 24/115 R |
| 2,611,501 A | | 7/1882 | Vandermark |
| 2,576,649 A | | 11/1951 | Slind |
| 2,856,933 A | | 10/1958 | Hildebrand et al. |

(Continued)

FOREIGN PATENT DOCUMENTS

DE    9 912 619    5/1954

(Continued)

OTHER PUBLICATIONS

*Patent Abstracts of Japan*, Abstract of Japanese Patent "Cranio-Knochenschallapen Fixing Device", Publication No. 05220174, Aug. 31, 1993, Japanese Application No. 04056619, Filed Feb. 10, 1992.

*Primary Examiner* — Pedro Philogene
(74) *Attorney, Agent, or Firm* — RatnerPrestia

(57) ABSTRACT

An implant is provided for fixing neighboring bone plates of the cranial bone in a simple and reliable manner. The implant comprises an outer bearing element for covering a spacing gap between the bone plates, which sits on outer surfaces of the bone plates. The outer bearing element has a first pair of outer openings and a first pair of inner openings. An inner bearing element is provided for covering the spacing gap between the bone plates, which sits on inner surfaces of the bone plates. The inner bearing element has a second pair of outer openings and a second pair of inner openings. A tensioning element is provided which is threaded through the openings of the outer and inner bearing elements in a displaceable manner, such that, when tensioned, the tensioning element draws the inner bearing element and the outer bearing element together.

28 Claims, 5 Drawing Sheets

U.S. PATENT DOCUMENTS

| | | | |
|---|---|---|---|
| 3,476,115 A | 11/1969 | Graeff et al. |
| 3,910,281 A | 10/1975 | Kletschka et al. |
| 4,177,813 A | 12/1979 | Miller et al. |
| 4,754,529 A | 7/1988 | Paradis |
| 4,765,329 A | 8/1988 | Cumming et al. |
| 4,802,477 A | 2/1989 | Gabbay |
| 4,966,600 A | 10/1990 | Songer et al. |
| 5,021,059 A | 6/1991 | Kensey et al. |
| 5,242,459 A | 9/1993 | Buelna |
| 5,250,049 A | 10/1993 | Michael |
| 5,258,011 A | 11/1993 | Drews |
| 5,350,399 A | 9/1994 | Erlebacher et al. |
| 5,423,858 A | 6/1995 | Bolanos et al. |
| 5,433,727 A | 7/1995 | Sideris |
| 5,454,821 A | 10/1995 | Harm et al. |
| 5,464,427 A | 11/1995 | Curtis |
| 5,466,241 A | 11/1995 | Leroy et al. |
| 5,527,341 A | 6/1996 | Gogolewski et al. |
| 5,549,620 A | 8/1996 | Bremer |
| 5,601,557 A | 2/1997 | Hayhurst |
| 5,707,373 A | 1/1998 | Sevrain et al. |
| 5,800,436 A | 9/1998 | Lerch |
| 5,868,746 A | 2/1999 | Sarver et al. |
| 5,919,205 A | 7/1999 | Heimberger et al. |
| 5,921,986 A | 7/1999 | Bonutti |
| 6,022,351 A | 2/2000 | Bremer et al. |
| 6,096,058 A | 8/2000 | Boche |
| 6,258,091 B1 | 7/2001 | Sevrain et al. |
| 6,270,500 B1 | 8/2001 | Lerch |
| 6,328,743 B2 * | 12/2001 | Lerch | 606/324 |
| 6,379,363 B1 * | 4/2002 | Herrington et al. | 606/79 |
| 6,589,244 B1 | 7/2003 | Sevrain et al. |
| 6,685,707 B2 | 2/2004 | Roman et al. |
| 6,726,688 B2 | 4/2004 | Lerch |
| 6,755,834 B2 * | 6/2004 | Amis | 606/916 |
| 6,921,401 B2 | 7/2005 | Lerch et al. |
| 7,048,737 B2 | 5/2006 | Wellisz |
| 7,238,188 B2 * | 7/2007 | Nesper et al. | 606/328 |
| 2002/0156475 A1 | 10/2002 | Lerch et al. |
| 2004/0210224 A1 | 10/2004 | Ahmad et al. |

FOREIGN PATENT DOCUMENTS

| | | |
|---|---|---|
| DE | 2 125 556 | 5/1971 |
| DE | 78 02 791 | 5/1978 |
| DE | 28 04 070 | 8/1979 |
| DE | 37 09 067 | 9/1988 |
| DE | 89 10 462.5 | 2/1990 |
| DE | 691 08 236 | 11/1991 |
| DE | 42 43 427 | 12/1992 |
| DE | 296 14 921 | 11/1996 |
| DE | 694 06 972 | 11/1997 |
| DE | 299 19 090 | 1/2000 |
| DE | 198 32 797 | 2/2000 |
| EP | 0 602 757 | 6/1994 |
| EP | 0 628 286 | 12/1994 |
| EP | 0787466 | 8/1997 |
| WO | WO 00/49949 | 8/2000 |

\* cited by examiner

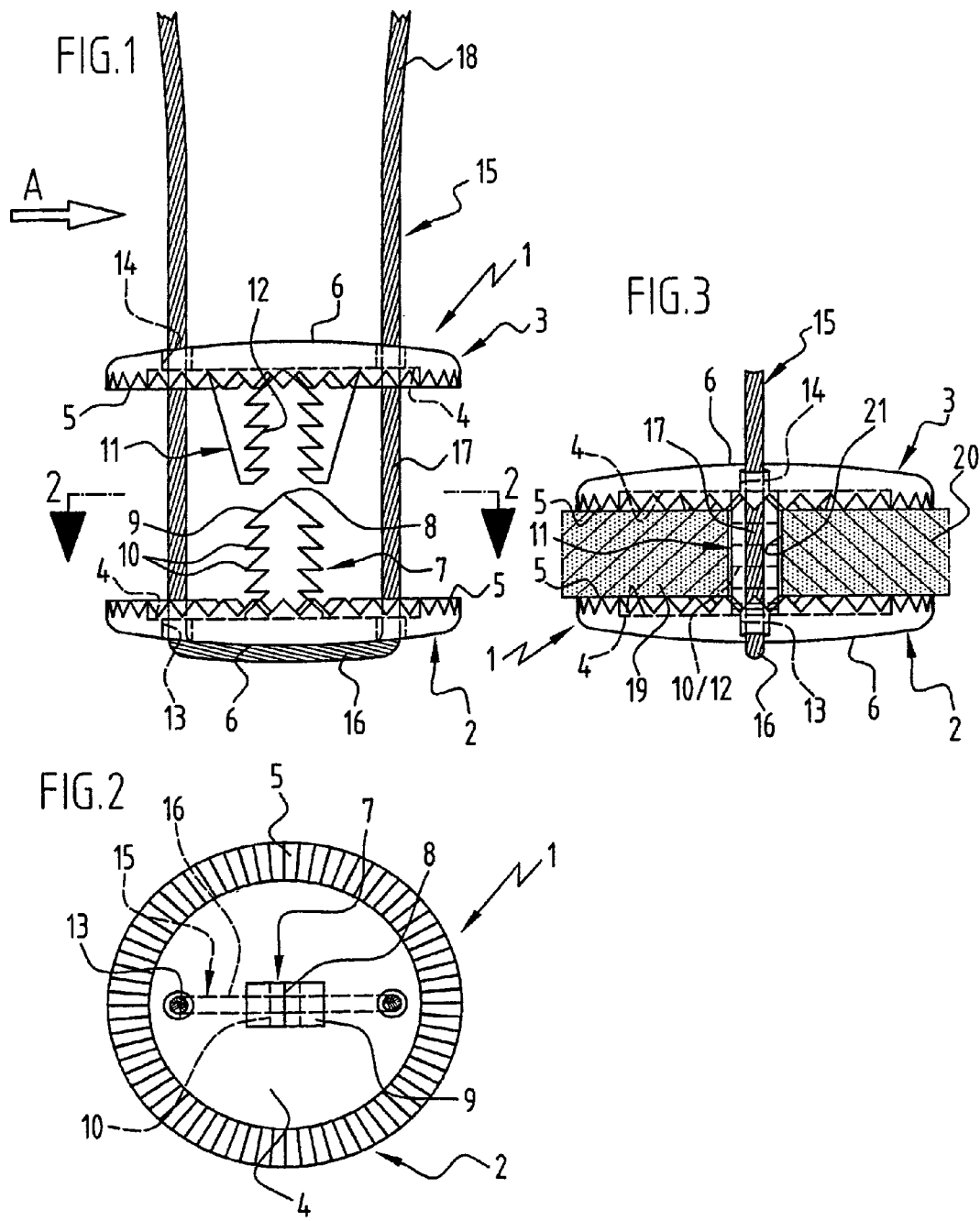

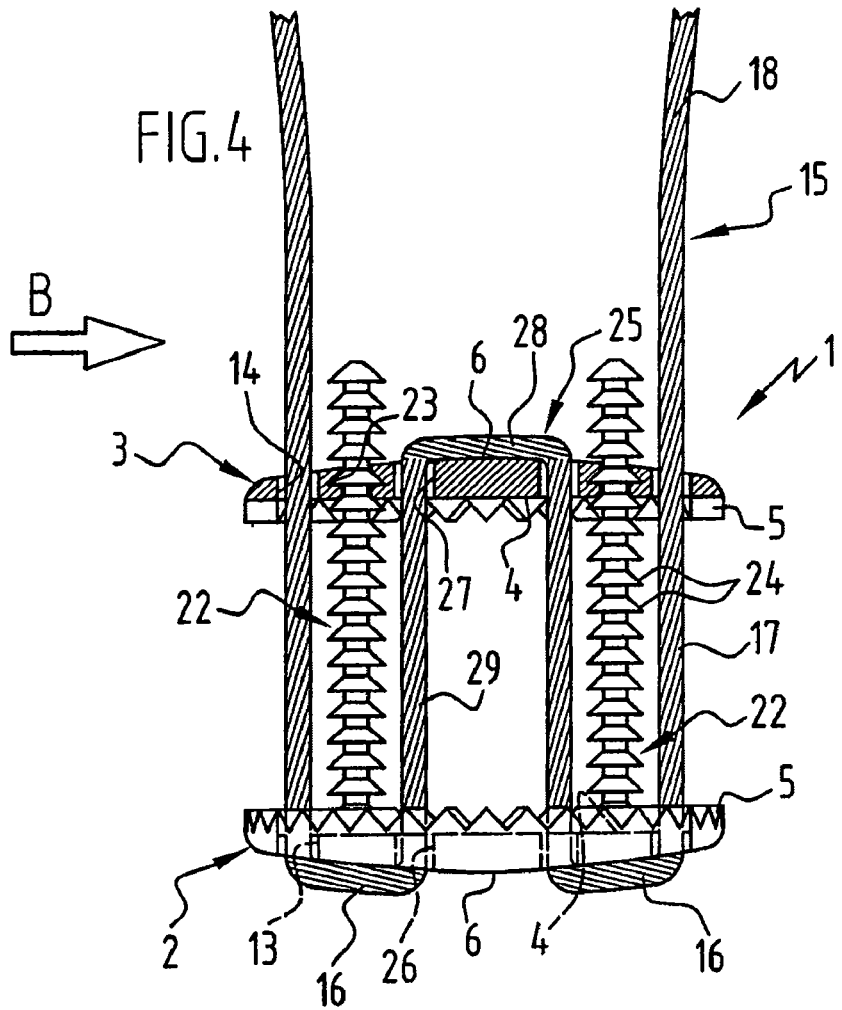
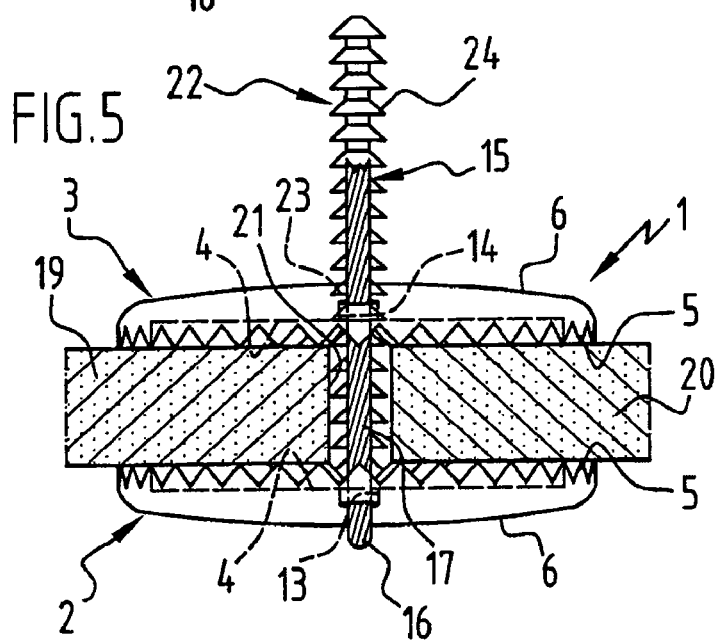

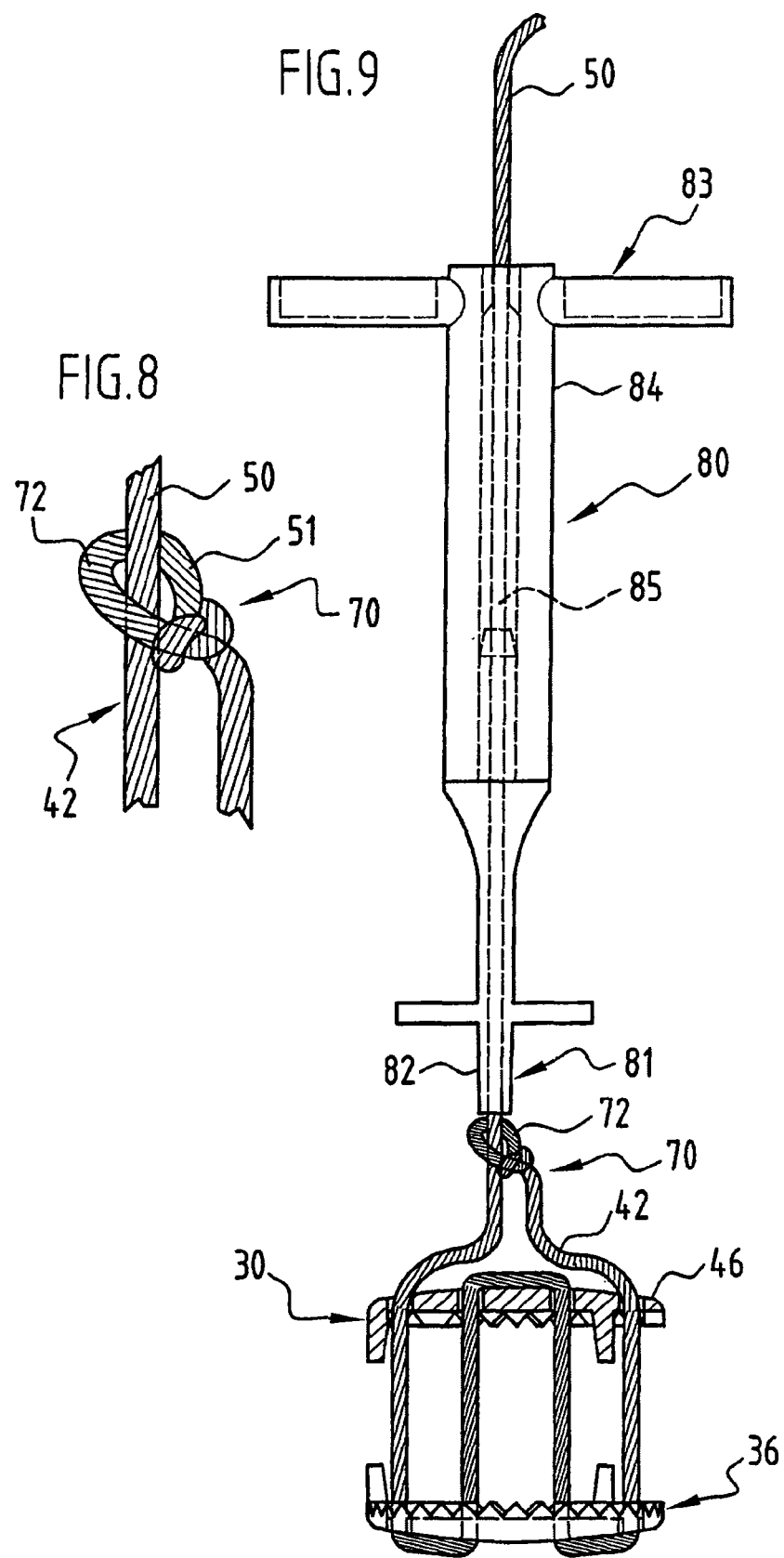

IMPLANT FOR FIXING BONE PLATES

CROSS-REFERENCE TO RELATED APPLICATIONS

This application is a continuation of U.S. application Ser. No. 10/911,982, filed Aug. 4, 2004, which is a continuation-in-part of U.S. application Ser. No. 10/718,851, filed Nov. 20, 2003, now U.S. Pat. No. 7,238,188, which is a continuation of International Patent Application PCT/EP02/05653, filed May 23, 2002, and claims the benefit of German Patent Application No. 101 28 917.0, filed Jun. 15, 2001, each of the foregoing applications being incorporated herein by reference in their entireties and for all purposes.

FIELD OF THE INVENTION

The invention relates to an implant for fixing neighboring bone plates of the cranial bone, wherein the plates have an inner surface and an outer surface. The implant comprises an inner bearing element which covers a spacing gap between the bone plates, an outer bearing element which covers the spacing gap, and a connecting device which extends through the spacing gap and which, when the bearing elements approach one another, connects the bearing elements together by means of a latching or a clamping connection in such a manner that they are no longer able to be moved apart.

BACKGROUND

Implants of this type are known from the German utility model 29919090 for example. They are used in order to relocate bone plates in their original position within the cranial bone after they have been separated therefrom by means of a saw cut so that they can graft back in this position.

For this purpose, it is known to arrange plate-like bearing elements on both sides of the bone plates, which are separated from one another by a spacing gap, and to connect them together by means of a central pin or a central locking strap. Moreover, rather than utilising latching or clamping means of this type, it is also known to simply draw the two plate-like bearing elements together by means of a thread-like tensioning element and to keep them clamped against one another by means of this thread-like tensioning element.

When using pin-like connecting means, it is necessary to clamp the two bearing elements together by means of a suitable tool which engages with the connecting device, which penetrates the outer bearing element and which simultaneously moves the outer bearing element along the connecting device in the direction of the inner bearing element. Such instruments are of complicated construction and are not always easy to manipulate.

If one uses a thread-like tensioning element for connecting the two bearing elements, then it is relatively easy to manipulate it when tensioning the bearing elements. However, this method results in a connection between the bearing elements which is very flexible and may sometimes give way in an undesirable manner in certain circumstances, for example, if the thread-like tensioning elements should work loose or if they dissolve in the case where a thread of resorbable material is being used.

SUMMARY OF THE INVENTION

In accordance with an example embodiment of the invention, an implant is provided for fixing neighboring bone plates of the cranial bone in a simple and reliable manner. The bone plates each have an inner surface and an outer surface. The implant comprises an outer bearing element for covering a spacing gap between the bone plates and which sits on the outer surfaces thereof. The outer bearing element has a first pair of outer openings and a first pair of inner openings. The implant further comprises an inner bearing element for covering the spacing gap between the bone plates and which sits on the inner surfaces thereof. The inner bearing element has a second pair of outer openings and a second pair of inner openings. A thread-like tensioning element is provided which is threaded through the openings of the outer and inner bearing elements in a displaceable manner, such that, when tensioned, the tensioning element draws the inner bearing element and the outer bearing element together. The tensioning element is threaded through the first pair of outer openings of the outer bearing element. The tensioning element is also threaded through the second pairs of outer and inner openings of the inner bearing element, such that the tensioning element extends over an outer surface of the inner bearing element that is remote from the outer bearing element. The tensioning element is further threaded through the first pair of inner openings of the outer bearing element, such that a loop is formed between the first pair of inner openings. The tensioning element is threaded in such a manner that the loop rests on an outer surface of the outer bearing element which is remote from the inner bearing element.

The tensioning element may rest on the inner bearing element between openings of the second pair of outer openings and neighboring openings of the second pair of inner openings. For example, the tensioning element may rest in two spaced resting portions on the inner bearing element.

Two ends of the tensioning element may be passed through the first pair of outer openings of the outer bearing element.

The first pair of outer openings of the inner bearing element may be spaced from one another by a distance which corresponds to at least half a length of the inner bearing element. Further, the openings of the first pair of inner openings of the outer bearing element and the openings of the second pair of inner openings of the inner bearing element may lie along a straight line. Likewise, the openings of first pair of outer openings of the outer bearing element and the openings of the second pair of outer openings of the inner bearing element may lie along a straight line.

When the bone plates are fixed in position by the tensioning element, the openings of the first pair of inner openings of the outer bearing element may be aligned with the openings of the second pair of inner openings of the inner bearing element. Similarly, once the bone plates are fixed in position, the openings of the first pair of outer openings of the outer bearing element may be aligned with the openings of the second pair of outer openings of the inner bearing element. Further, when the bone plates are fixed in position, sections of the tensioning element extending between the bearing elements and the loop may be arranged in a plane.

The second pair of inner openings of the inner bearing element and the second pair of outer openings of the inner bearing element may be mutually equidistant. The first pair of inner openings of the outer bearing element and the first pair of outer openings of the outer bearing element may be mutually equidistant.

The second pair of inner openings of the inner bearing element may comprise two mutually spaced openings.

The tensioning element may comprise a material that is absorbable in the body.

The tensioning element, when threaded through the inner and outer bearing elements, may form a pulley and block system for drawing the inner and outer bearing elements together.

In a further example embodiment of the present invention, the tensioning element may be secured by a knot after it is tensioned and the inner and outer bearing elements are drawn together. In such an embodiment, the tensioning element may further comprise a pre-formed slip-knot which forms a loop at one end of the tensioning element. A free end of the tensioning element may be fed through the openings of the inner and outer bearing elements and through the loop formed by the slip-knot. Tension may then be applied to the tensioning element by drawing the free end through the loop. An applicator may be used to tension the tensioning element by holding the free end of the tensioning element while displacing the knot towards the outer bearing element.

Serrated regions may be provided on respective outer edges of inner surfaces of at least one of the bearing elements. In addition, at least one distancing peg extending from a respective inner surface of at least one bearing element may be provided for maintaining a gap between the neighboring bone plates. The at least one distancing peg may be aligned with the openings of the corresponding bearing element.

In an example embodiment, at least one of the bearing elements may comprise a first peg and a second spaced peg. The first peg may be arranged at or close to an outer edge of the corresponding bearing element.

The tensioning element may have four spaced tensioning element portions extending between the inner bearing element and the outer bearing element. In such an embodiment, the loop resting on the outer surface of the outer bearing element may be arranged between inner tensioning element portions extending between the inner bearing element and the outer bearing element.

BRIEF DESCRIPTION OF THE DRAWINGS

The present invention will hereinafter be described in conjunction with the appended drawing figures, wherein like reference numerals denote like elements, and:

FIG. 1: a side view of a first exemplary embodiment of an implant incorporating a U-shaped thread-like tensioning element and having latching projections directed towards the respective other bearing element prior to the bearing elements being brought together FIG. 2: a sectional view along the line 2-2 in FIG. 1;

FIG. 3: a view of the implant of FIG. 1 in the direction of the arrow A in FIG. 1 after the application of the implant to two bone plates;

FIG. 4: a view similar to FIG. 1 of a further exemplary embodiment of an implant comprising two mutually spaced connecting devices and a thread-like tensioning element in a multiple loop arrangement;

FIG. 5: a view of the implant of FIG. 4 in the direction of the arrow B in FIG. 4 after the application of the implant to two bone plates;

FIG. 8: a view of an example embodiment of a pre-formed slip-knot used to secure the thread-like tensioning element shown in the embodiment of FIG. 6;

FIG. 9: a view of an example embodiment of an applicator which may be used to tension the tensioning element shown in the embodiment of FIG. 6;

DETAILED DESCRIPTION OF EMBODIMENTS OF THE INVENTION

Figure 6:
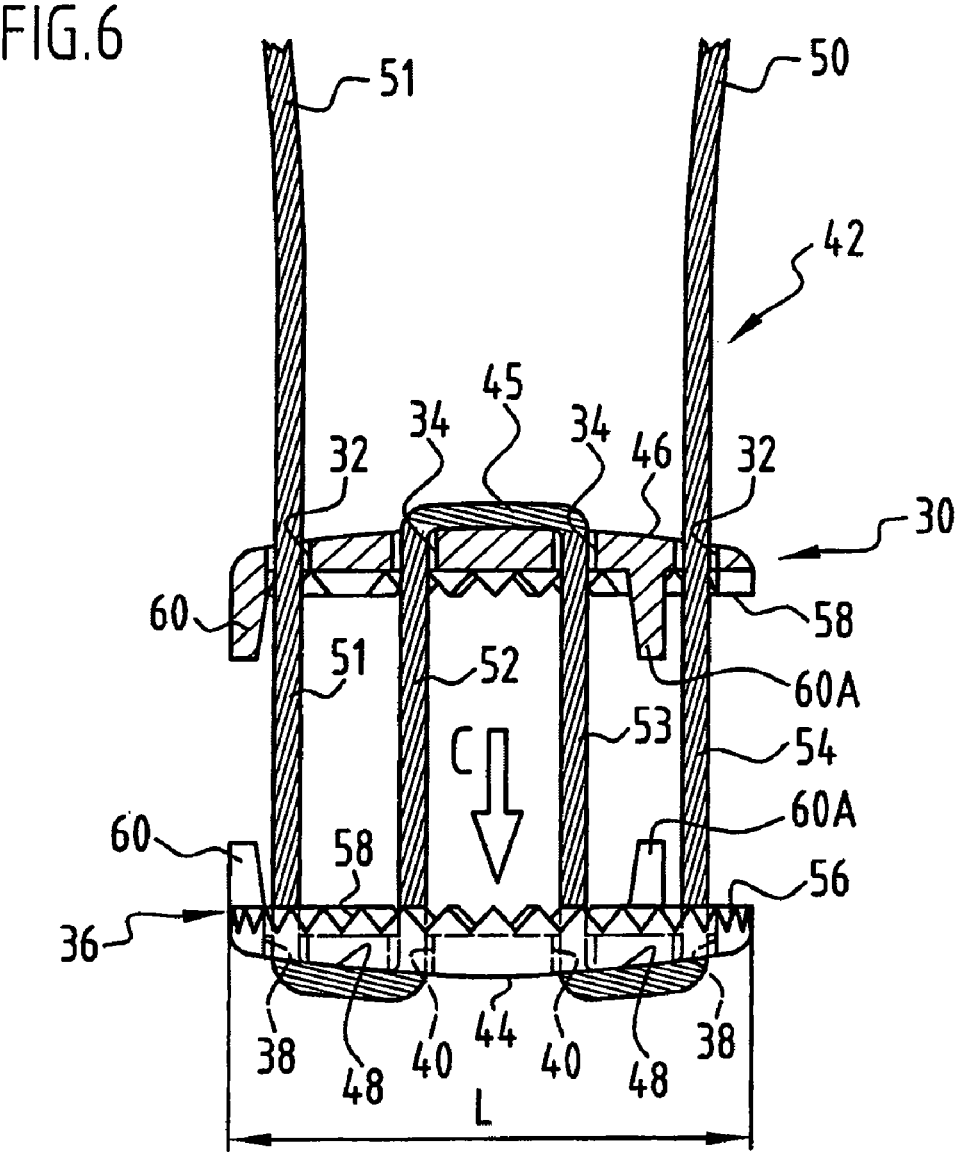
FIG. 6: a side view of another exemplary embodiment of an implant comprising inner and outer bearing elements connected by a thread-like tensioning element.
Figure 7:
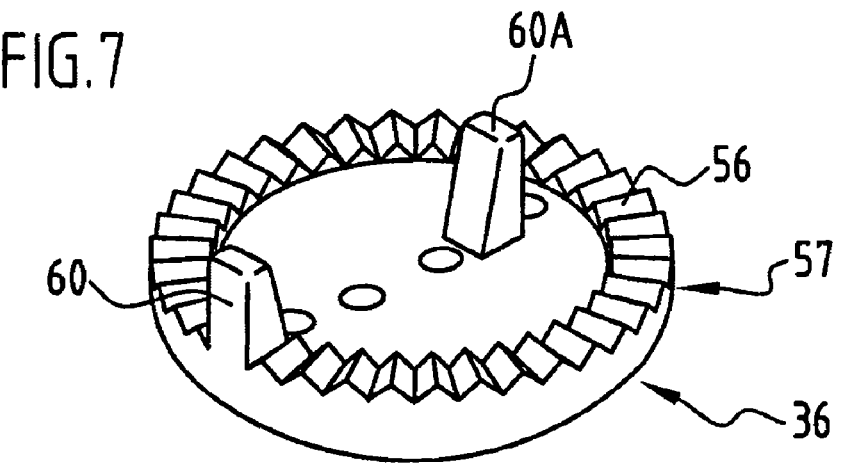
FIG. 7: a perspective view of the inner bearing element in the direction of the arrow C in FIG. 6.

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The implant 1 illustrated in FIGS. 1 to 3 incorporates two circular, plate-like bearing elements 2, 3 which comprise a serrated boundary region 5 on the flat, mutually facing inner faces 4 thereof and an external surface 6 which is slightly domed in the outward direction.

The inner bearing element 2 carries a central latching projection 7 which points towards the outer bearing element 3 and has a tip 8 with inclined glide surfaces 9. This latching projection 7 has an elongated rectangular cross section and the narrow sides thereof carry a number of latches 10, while the broad sides thereof are smoothly formed.

The outer bearing element 3 carries two mutually spaced latching projections 11 which point towards the inner bearing element 2 and are likewise provided with a number of latches 12 on the mutually facing narrow sides. These narrow sides incorporating the latches 12 are spaced from one another by a distance which corresponds to the width of the latching projections 7 on the inner bearing element 2. When the two bearing elements 2, 3 are moved close to one another, the free ends of the latching projections 11 slide on the inclined glide surfaces 9 of the latching projections 7 and are slightly flexed apart so that the latches 12 can slide past the latches 10. The shaping of the latches 10 and 12 is selected in such a way that although it is possible for the bearing elements 2 and 3 to come close together, the two bearing elements 2, 3 will not be able to separate from each other following the engagement of the latches 10 and 12.

The latching projections 11 are also of rectangular cross-section and are provided with latch-free broad sides and narrow sides which carry the latches 12 in like manner to the latching projection 7. The latching projections 7 and 11 thus extend substantially in a plane which runs parallel to the broad sides of the latching projections 7 and 11, but they are of very small dimensions in the transverse direction, as is clear from the illustration in FIG. 3.

In this plane spanned by the latching projections 7 and 11, there are provided two openings 13 and 14 which penetrate the respective bearing elements, both the inner bearing element 2 and the outer bearing element 3. These openings 13 and 14 are mutually spaced by a distance which corresponds to at least the radius of the bearing elements 2, 3 and are arranged symmetrically relative to the two sides of the respective latching projections 7 and 11. A thread-like tensioning element 15 is fed through these openings 13, 14 in such a manner that a central section 16 will rest against the outer surface 6 of the bearing element 2 between the openings 13 in the inner bearing element 2. Two connecting sections 17 of the tensioning element 15 will extend in parallel with the latching projection 7 from each opening 13 in the inner bearing element 2 to each opening 14 in the outer bearing element 3. Two ends 18 of the tensioning element 15 extend through the openings 14 and continuing over the outer surface 6 of the outer bearing element 3 (FIG. 1).

The two bearing elements 2 and 3 preferably consist of a body-compatible synthetic material, whilst the latching projections 7 and 10 are formed in one-piece with the respective bearing elements 2 and 3. The thread-like tensioning element 15 may be a conventional surgical thread, it being expedient if it consists of an absorbable material which gradually decomposes after insertion into the body.

The described implant 1 serves for fixing two bone plates 19, 20 of the cranial bone which are to be fixed directly adjacent one another while leaving a spacing gap 21 therebetween. The spacing gap 21 is usually a saw-slot which is formed as a result of a bone plate being sawn out from the cranial bone. Consequently, one of the two bone plates is usually the solid bone plate of the skull, while the other bone plate is a sawn-out cranial bone which allowed access to be made to the brain. As is apparent from FIG. 1, for the purposes of fixing the two bone plates to one another, the implant 1 is firstly advanced towards a bone plate in such a way that the inner bearing element 2 will come to rest against the inner surface of the bone plate. The other bone plate is then introduced laterally into the intermediary space between the two bearing elements 2, 3 which are still spaced from one another. The inner bearing element 2 is then clamped against the inner faces of the two bone plates 19, 20 with the help of the tensioning element 15. When the inner bearing element 2 is fixed in position, the outer bearing element 3 is pushed towards the inner bearing element 2 until such time as the respective latches 10 and 12 of the two latching projections 7 and 11 come into engagement with one another. This process of advancing the outer bearing element 3 can either be effected manually or by utilising an instrument, whereby the inner bearing element 2 will be held in place on the inner surface of the bone plates with the help of the tensioning element 15, or else by virtue of the two ends of the tensioning element 15 being drawn together, for example, by means of a known tensioning knot which is adapted to effect a shortening of the tensioning element 15 in the form of a loop extending through the openings 13 and 14, but not however, a prolongation thereof.

The latching projections 7 and 10 lie in the same plane as that in which the connecting sections 17 of the tensioning element 15 also extend, the dimensions of each of the parts in a direction transverse to this plane being very small so that these parts will easily fit into even a very narrow spacing gap 21, as is clear from the illustration in FIG. 3. At the same time, the latching projections 7 and 11 as well as the central section 17 of the tensioning element 15 will orient the two bearing elements 2, 3 in such a way that this plane runs parallel to the spacing gap 21.

If the two bearing elements 2, 3 are clamped together in this way, they can then be securely held in this seating position, which is illustrated in FIG. 3, by the engagement of the latches 10 and 12. The tensioning element 15 can then either be removed by simply pulling it out of the openings 13, 14, or, it may be left in place as an additional security device, whereby it is expedient to knot the two ends 18 to one another.

In the case of the implant illustrated in FIGS. 1 to 3, the connecting means of the two bearing elements 2, 3 formed by the latching projections 7 and 11 do not project through the bearing elements, but rather, they merely extend through the space in the spacing gap 21.

This is not the case in the exemplary embodiment of an implant illustrated in FIGS. 4 and 5, although this implant is of similar construction and the mutually corresponding parts thereof bear the same reference symbols. In the case of the implant in FIGS. 4 and 5, the inner bearing element 2 has two mutually spaced, parallel connecting pins 22 which extend symmetrically relative to the center point and protrude through apertures 23 in the outer bearing element 3. The connecting pins 22 carry peripheral latching ribs 24 which are beveled at one side and can be pushed through the apertures 23 in one direction. In the opposite direction, the latching ribs engage and latch behind the edges of the apertures 23 in such a manner that it is no longer possible to pull the bearing elements 2 and 3 apart. The edges of the apertures 23 are thus latching projections which co-operate with the latching ribs 24.

The connecting pins 22 are arranged in the plane which is defined by the openings 13 and 14 for the tensioning element 15. The connecting pins 22 are of very small diameter so that they exhibit only a very small dimension in a direction transverse to this plane and thus the implant 1, together with the tensioning element 15 and the two connecting pins 22, can also be fitted into a very narrow spacing gap 21.

Moreover, in the case of the exemplary embodiment of FIGS. 4 and 5, the central area of the tensioning element 15 is in the form of an additional loop 25, thus deviating from the shape of the implant depicted in FIGS. 1 to 3. Namely, this loop 25 passes through two openings 26 located between the openings 13 in the inner bearing element 2 and through two openings 27 arranged between the openings 14 in the outer bearing element 3, so that the central section 28 of this loop 25 rests on the outer surface 6 of the outer bearing element 3. The openings 26 and 27 are thereby located closer to the center of the respective bearing elements 2 and 3 than the apertures 23 so that two further connecting elements 29 now extend between the two connecting pins 22 in addition to the connecting sections 17 of the tensioning element 15. The connecting elements 29 form the legs of the loop 25 and lie in the same plane as the connecting sections 17 and the connecting pins 22. This thereby results in a pulley-block-like guidance of the tensioning element 15 so that, when tensioning the latter, the displacement path of the bearing elements 2, 3 will be scaled down with respect to the tensioning path of the tensioning element 15.

This guidance of the tensioning element 15 is particularly advantageous in an arrangement comprising two mutually spaced connecting means such as is formed by the connecting pins 22, but use could also easily be made of differently constructed bearing elements 2, 3 wherein other forms of connecting means are provided.

It is also expedient in the case of the exemplary embodiment depicted in FIGS. 4 and 5, if the connecting pins 22 are formed in one-piece with the bearing elements 2, 3, whereby these preferably consist of a body-compatible synthetic material. As discussed above in connection with the example embodiment of FIGS. 1-3, the tensioning element 15 may be made of an absorbable material.

Figure 10:
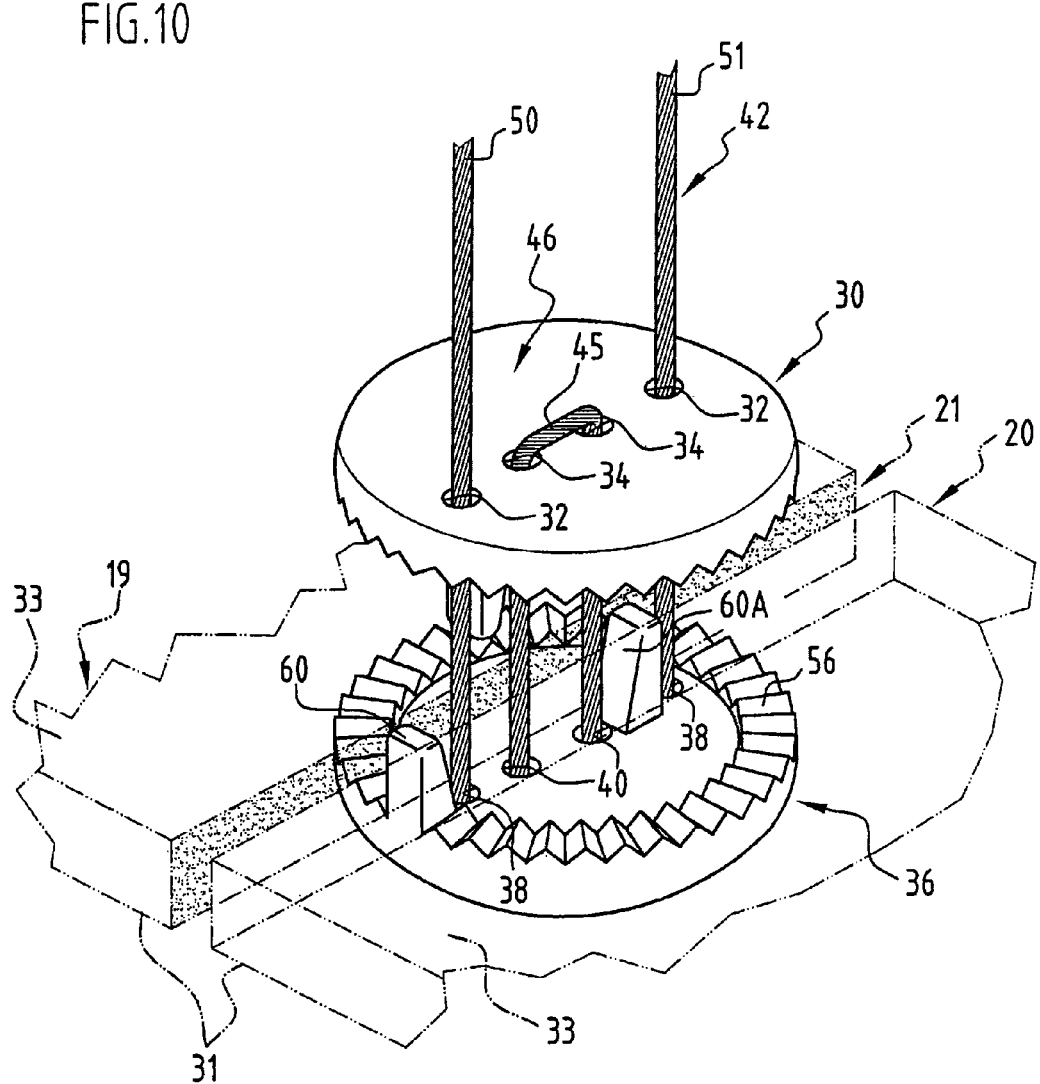
FIG. 10: a perspective view of the implant of FIG. 6 being applied to two bone plates.

A further example embodiment of an implant for fixing neighboring bone plates 19, 20 of the cranial bone is shown in FIGS. 6-10. The bone plates 19, 20 each have an inner surface 31 and an outer surface 33 (FIG. 10). The implant comprises an outer bearing element 30 for covering a spacing gap 21 between the bone plates 19, 20 and which sits on the outer surfaces 33 thereof. The outer bearing element 30 has a first pair of outer openings 32 and a first pair of inner openings 34. The implant further comprises an inner bearing element 36 for covering the spacing gap 21 between the bone plates 19, 20 and which sits on the inner surfaces 31 thereof. The inner bearing element 36 has a second pair of outer openings 38 and a second pair of inner openings 40. A thread-like tensioning element 42 is provided which is threaded through the openings 32, 34, 38, and 40 of the outer and inner bearing elements 30 and 36 in a displaceable manner, such that, when tensioned, the tensioning element 42 draws the inner bearing element 36 and the outer bearing element 30 together.

The tensioning element 42 shown in FIG. 6 is threaded through the inner and outer bearing elements 30 and 36 in a manner similar to that described above with respect to the threading of tensioning element 15 through bearing elements 2 and 3 in connection with FIG. 4. However, with the embodiment shown in FIG. 6, no additional connecting means are required.

The tensioning element 42 is threaded through the first pair of outer openings 32 of the outer bearing element 30. The tensioning element 42 is also threaded through the second pairs of outer and inner openings 38, 40 of the inner bearing element 36, such that the tensioning element 42 extends over an outer surface 44 of the inner bearing element 36 that is remote from the outer bearing element 30. The tensioning element 42 is further threaded through the first pair of inner openings 34 of the outer bearing element 30, such that a loop 45 is formed between the first pair of inner openings 34. The tensioning element 42 is threaded in such a manner that the loop 45 rests on an outer surface 46 of the outer bearing element 30 which is remote from the inner bearing element 36.

The tensioning element 42 may rest on the inner bearing element 36 between openings of the second pair of outer openings 38 and neighboring openings of the second pair of inner openings 40. For example, the tensioning element 42 may rest in two spaced resting portions 48 on the inner bearing element 36.

Two ends 50, 51 of the tensioning element 42 may be passed through the first pair of outer openings 32 of the outer bearing element 30. These ends 50, 51 may be used to tension the tensioning element 42, thereby drawing the bearing elements 30, 36 together. The ends 50, 51 may also be used to secure the bearing elements 30, 36 together, as described in further detail below.

The first pair of outer openings 38 of the inner bearing element 36 may be spaced from one another by a distance which corresponds to at least half a length L of the inner bearing element 36. Further, the openings of the first pair of inner openings 34 of the outer bearing element 30 and the openings of the second pair of inner openings 40 of the inner bearing element 36 may lie along a straight line. Likewise, the openings of first pair of outer openings 32 of the outer bearing element 30 and the openings of the second pair of outer openings 38 of the inner bearing element 36 may lie along a straight line.

The tensioning element 42 may have four spaced tensioning element portions 51, 52, 53, and 54 extending between the inner bearing element 36 and the outer bearing element 30. In such an embodiment, the loop 45 resting on the outer surface 46 of the outer bearing element 30 may be arranged between inner tensioning element portions 52, 53 extending between the inner bearing element 36 and the outer bearing element 30.

The tensioning element 42, when threaded through the inner and outer bearing elements 30, 36, may form a pulley and block system for drawing the inner and outer bearing elements 30, 36 together, similar to that discussed above in connection with FIG. 4.

When the bone plates 19, 20 are fixed in position by the tensioning element 42, the openings of the first pair of inner openings 34 of the outer bearing element 30 may be aligned with the openings of the second pair of inner openings 40 of the inner bearing element 36. Similarly, once the bone plates 19, 20 are fixed in position, the openings of the first pair of outer openings 32 of the outer bearing element 30 may be aligned with the openings of the second pair of outer openings 38 of the inner bearing element 36. Further, when the bone plates 19, 20 are fixed in position, sections 51, 52, 53, and 54 of the tensioning element 42 extending between the bearing elements 30, 36 and the loop 45 may be arranged in a plane.

The second pair of inner openings 40 of the inner bearing element 36 and the second pair of outer openings 38 of the inner bearing element 36 may be mutually equidistant. The first pair of inner openings 34 of the outer bearing element 30 and the first pair of outer openings 32 of the outer bearing element 30 may be mutually equidistant.

The second pair of inner openings 40 of the inner bearing element 36 may comprise two mutually spaced openings.

The tensioning element 42 may comprise a material that is absorbable in the body.

Serrated regions 56 may be provided on respective outer edges 57 of inner surfaces 58 of at least one of the bearing elements 30, 36. In addition, at least one distancing peg 60 extending from a respective inner surface 58 of at least one bearing element 30, 36 may be provided for maintaining a gap between the neighboring bone plates 19, 20. The at least one distancing peg 60 may be aligned with the openings 32, 34, 38, 40 of the corresponding bearing element 30, 36.

In an example embodiment, at least one of the bearing elements 30, 36 may comprise a first peg 60 and a second spaced peg 60A. The first peg 60 may be arranged at or close to an outer edge 57 of the corresponding bearing element 30, 36. The distancing pegs 60, 60A and the openings 32, 34, 38, and 40 may all be arranged in a plane so that the distancing pegs 60, 60A and the openings 32, 34, 38, and 40 extend through the same spacing gap 21 when fixed in position on the bone plates 19 and 20.

In a further example embodiment of the present invention, the tensioning element 42 may be secured by a knot after it is tensioned and the inner and outer bearing elements 30, 36 are drawn together. In such an embodiment, the tensioning element 42 may further comprise a pre-formed slip-knot 70 as shown in FIG. 8, which forms a loop 72 at one end 51 of the tensioning element 42. Such a slip-knot 70 may comprise any type of displaceable or sliding knot, including but not limited to a Roeder knot, a Duncan knot, a Tennessee Slider, or modified versions of the foregoing knots now known or to be developed. A free end 50 of the tensioning element 42 may be fed through the openings of the inner and outer bearing elements 32, 34, 38, 40 and through the loop 72 formed by the slip-knot 70. Tension may then be applied to the tensioning element 42 by drawing the free end 50 through the loop 72.

As shown in FIG. 9, an applicator 80 may be used to tension the tensioning element 42 by holding the free end 50 of the tensioning element 42 while displacing the knot 70 towards the outer surface 46 of the bearing element 30. The applicator 80 may comprise a displacement element 81 at a distal end 82 thereof and a gripping element 83 at a proximal end 84 thereof. The displacement element 81 may be in the form of a sleeve. A through opening 85 is provided which passes through the entire length of the applicator 80. The free end 50 of the tensioning element 42 is passed through the through opening 85 and is freely displaceable therein. By holding or pulling the free end 50 of the tensioning element 42 while at the same time displacing the displacement element 81 by means of the gripping element 83, the knot 70 may be displaced towards the outer surface 46 of the outer bearing element 30. A holding element, such as a ring (not shown) may be secured to the free end 50 of the tensioning element 42 to enable an operator to easily grip the free end 50 of the tensioning element 42.

Additional details regarding an example embodiment of an applicator which may be used with the implant of the present invention are described in commonly owned co-pending U.S. patent application Ser. No. 10/862,788 filed on Jun. 7, 2004, which is incorporated herein and made a part hereof by reference for all purposes.

Although the invention has been described in connection with various exemplary embodiments thereof, those skilled in the art will appreciate that numerous adaptations and modifications may be made thereto without departing from the spirit and scope of the invention, as set forth in the following claims.

What is claimed is:

1. An implant for fixing neighboring bone plates of the cranial bone, said plates having an inner surface and an outer surface, the implant comprising:
    an outer bearing element for covering a spacing gap between the bone plates, said outer bearing element having a first pair of outer openings and a first pair of inner openings; and
    an inner bearing element for covering the spacing gap, said inner bearing element having a second pair of outer openings and a second pair of inner openings;
    a tensioning element threaded through the openings of the outer and inner bearing elements in a displaceable manner; wherein:
    when tensioned, the tensioning element draws the inner bearing element and the outer bearing element together;
    the tensioning element is threaded through the first pair of outer openings of the outer bearing element;
    the tensioning element is threaded through the second pairs of outer and inner openings of the inner bearing element and extends over an outer surface of the inner bearing element that is remote from the outer bearing element; and
    the tensioning element is threaded through the first pair of inner openings of the outer bearing element, forming a loop between said first pair of inner openings, said loop resting on an outer surface of the outer bearing element which is remote from the inner bearing element.

2. An implant in accordance with claim 1, wherein the tensioning element rests on the inner bearing element between openings of the second pair of outer openings and neighboring openings of the second pair of inner openings.

3. An implant in accordance with claim 2, wherein the tensioning element rests in two spaced resting portions on the inner bearing element.

4. An implant in accordance with claim 1, wherein two ends of the tensioning element are passed through the first pair of outer openings of the outer bearing element.

5. An implant in accordance with claim 1, wherein the first pair of outer openings of the inner bearing element are spaced from one another by a distance which corresponds to at least half a length of the inner bearing element.

6. An implant in accordance with claim 1, wherein the openings of the first pair of inner openings of the outer bearing element and the openings of the second pair of inner openings of the inner bearing element lie along a straight line.

7. An implant in accordance with claim 1, wherein the openings of first pair of outer openings of the outer bearing element and the openings of the second pair of outer openings of the inner bearing element lie along a straight line.

8. An implant in accordance with claim 1, wherein when the bone plates are fixed in position:
    the openings of the first pair of inner openings of the outer bearing element are aligned with the openings of the second pair of inner openings of the inner bearing element; and
    the openings of the first pair of outer openings of the outer bearing element are aligned with the openings of the second pair of outer openings of the inner bearing element.

9. An implant in accordance with claim 1, wherein the second pair of inner openings of the inner bearing element and the second pair of outer openings of the inner bearing element are mutually equidistant.

10. An implant in accordance with claim 1, wherein the first pair of inner openings of the outer bearing element and the first pair of outer openings of the outer bearing element are mutually equidistant.

11. An implant in accordance with claim 1, wherein the second pair of inner openings of the inner bearing element comprise two mutually spaced openings.

12. An implant in accordance with claim 1, wherein when the bone plates are fixed in position the sections of the tensioning element extending between the bearing elements and the loop are arranged in a plane.

13. An implant in accordance with claim 1, wherein the tensioning element comprises a material that is absorbable in the body.

14. An implant in accordance with claim 1, wherein the tensioning element, when threaded through the inner and outer bearing elements, forms a pulley and block system for drawing the inner and outer bearing elements together.

15. An implant in accordance with claim 1, wherein, after tensioning, the tensioning element is secured by a knot.

16. An implant in accordance with claim 1, wherein the tensioning element further comprises a pre-formed slip-knot forming a loop at one end of the tensioning element.

17. An implant in accordance with claim 16, wherein a free end of the tensioning element is fed through the openings of said inner and outer bearing elements and through the loop formed by said slip-knot.

18. An implant in accordance with claim 17, wherein the tension is applied to the tensioning element by drawing said free end through said loop.

19. An implant in accordance with claim 18, wherein an applicator is used to tension the tensioning element by holding said free end of said tensioning element while displacing the knot towards the outer bearing element.

20. An implant in accordance with claim 1, further comprising:
    serrated regions on respective outer edges of inner surfaces of at least one of said bearing elements.

21. An implant in accordance with claim 1, further comprising:
    at least one distancing peg extending from a respective inner surface of at least one bearing element for maintaining a gap between said neighboring bone plates.

22. An implant in accordance with claim 21, wherein said at least one distancing peg is aligned with said openings of the corresponding bearing element.

23. An implant in accordance with claim 21, wherein at least one of the bearing elements comprises a first peg and a second spaced peg.

24. An implant in accordance with claim 23, wherein the first peg is arranged at or close to an outer edge of the corresponding bearing element.

25. An implant in accordance with claim 1, wherein the tensioning element has four spaced tensioning element portions extending between the inner bearing element and the outer bearing element.

26. An implant in accordance with claim 25, wherein the loop resting on the outer surface of the outer bearing element is arranged between inner tensioning element portions extending between the inner bearing element and the outer bearing element.

27. An implant for fixing neighboring bone plates of the cranial bone, said plates having an inner surface and an outer surface, the implant comprising:
   an outer bearing element for covering a spacing gap between the bone plates, said outer bearing element having a first pair of outer openings and a first pair of inner openings;
   an inner bearing element for covering the spacing gap, said inner bearing element having a second pair of outer openings and a second pair of inner openings; and
   a tensioning element threaded through the openings of the outer and inner bearing elements in a displaceable manner and drawing the inner bearing element and the outer bearing element together, the tensioning element being threaded through the first pair of outer openings of the outer bearing element, through the second pairs of outer and inner openings of the inner bearing element, extending over an outer surface of the inner bearing element that is remote from the outer bearing element, and further being threaded through the first pair of inner openings of the outer bearing element, forming a loop between said first pair of inner openings, said loop resting on an outer surface of the outer bearing element which is remote from the inner bearing element such that the tensioning element is symmetrically arranged through the inner and outer bearing elements.

28. An implant for fixing neighboring bone plates of the cranial bone, said plates having an inner surface and an outer surface, the implant comprising:
   an outer bearing element for covering a spacing gap between the bone plates, said outer bearing element having a first pair of outer openings and a first pair of inner openings;
   an inner bearing element for covering the spacing gap, said inner bearing element having a second pair of outer openings and a second pair of inner openings; and
   a tensioning element extending through the openings of the outer and inner bearing elements to couple the inner bearing element and the outer bearing element together, the tensioning element extending through the first pair of outer openings of the outer bearing element, and through the second pairs of outer and inner openings of the inner bearing element, the tensioning element extending over an outer surface of the inner bearing element that is remote from the outer bearing element such that the tensioning element forms a first loop and a second loop extending over the outer surface of the inner bearing element remote from the outer bearing element, the tensioning element further extending through the first pair of inner openings of the outer bearing element, forming a third loop between said first pair of inner openings, said third loop extending over an outer surface of the outer bearing element remote from the inner bearing element.

* * * * *

UNITED STATES PATENT AND TRADEMARK OFFICE
CERTIFICATE OF CORRECTION

PATENT NO. : 8,048,130 B2
APPLICATION NO. : 12/512412
DATED : November 1, 2011
INVENTOR(S) : Markus Nesper et al.

Page 1 of 1

It is certified that error appears in the above-identified patent and that said Letters Patent is hereby corrected as shown below:

On the title page, the Foreign Application Priority Data should be added as follows:

-- (30) Application Priority Data June 15, 2001 (DE) 101 28 917.0 --

Signed and Sealed this
Seventeenth Day of January, 2012

David J. Kappos
*Director of the United States Patent and Trademark Office*